United States Patent [19]

Yoshimura et al.

[11] 4,053,466
[45] Oct. 11, 1977

[54] (E)-2-[P-(β-SUBSTITUTED-VINYL)PHENYL]-ALKANOIC ACIDS

[75] Inventors: Shoji Yoshimura, Chofu; Susumu Takahashi, Hachioji; Motonobu Ichino; Tokuro Nakamura, both of Mitaka, all of Japan

[73] Assignee: Kohjin Co., Ltd., Tokyo, Japan

[21] Appl. No.: 727,484

[22] Filed: Sept. 28, 1976

Related U.S. Application Data

[63] Continuation-in-part of Ser. No. 594,461, July 9, 1975, abandoned.

[30] Foreign Application Priority Data

July 9, 1974 Japan .................................. 49-77782

[51] Int. Cl.² .................. C07D 307/26; C07D 307/28; C07D 333/10; C07D 333/12
[52] U.S. Cl. ................................ 542/454; 260/347.3; 260/329 F
[58] Field of Search ............. 260/240 D, 347.3, 329 F

[56] References Cited

U.S. PATENT DOCUMENTS 2,526,319 10/1950 Beatty ...................... 260/329 F UX
3,473,656 7/1973 Brown et al. .................. 260/347.3 X

OTHER PUBLICATIONS

Yoshina et al., "2-(2Furyl Vinylbexan", in J. Pharm. Soc. Japan, vol. 88 (1968) pp. 410–416.

Primary Examiner—Allen B. Curtis
Attorney, Agent, or Firm—Sughrue, Rothwell, Mion, Zinn, and Macpeak

[57] ABSTRACT (E)-2-[p-(β-Substituted-vinyl)phenyl]alkanoic acids represented by the formula (I):

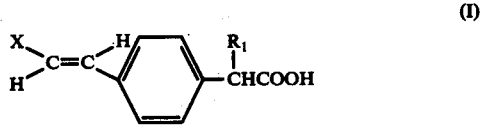

wherein $R_1$ and X are as hereinafter defined, having anti-inflammatory, analgesic, antipyretic and platelet aggregation inhibitory activities.

10 Claims, No Drawings

(E)-2-[P-(β-SUBSTITUTED-VINYL)PHENYL]ALK- ANOIC ACIDS

CROSS REFERENCE TO RELATED APPLICATIONS

This application is a continuation-in-part application of copending application Ser. No. 594,461, filed July 9, 1975, now abandoned.

BACKGROUND OF THE INVENTION

1. Field of the Invention

This invention relates to novel (E)-2-[p-(β-substituted-vinyl)phenyl]alkanoic acids having anti-inflammatory, analgesic, antipyretic and platelet aggregation inhibitory activities.

2. Description of the Prior Art

It has hitherto been known that 4-stilbene-acetic acid has an anti-chlolesterinemic activity (e.g., as described in G. Cavallini and E. Massarani, *Farmaco. Edizione Scientifica*, 11, 167 (1956)). However, the compounds having the formula (I) above and exhibiting anti-inflammatory, analgesic, antipyretic andl platelet aggregation inhibitory activities are not disclosed in the prior art.

SUMMARY OF THE INVENTION

An object of the present invention is to provide (E)-2-[p-(β-substituted-vinyl)phenyl]alkanoic acids having anti-inflammatory, analgesic, antipyretic and platelet aggregation inhibitory activities.

Accordingly, this invention provides (E)-2-[p-(β-substituted-vinyl)phenyl]alkanoic acids represented by the formula (I):

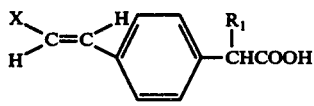

(I)

wherein $R_1$ represents a hydrogen atom, a methyl group or an ethyl group; and X represents a

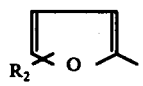

group or a

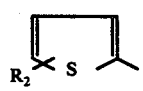

group, wherein $R_2$ represents a hydrogen atom, a nitro group, an amino group, a hydroxyl group, a halogen atom, an alkyl group having 1 to 4 carbon atoms, or an alkoxy group having 1 to 4 carbon atoms, and the pharmaceutically acceptable salts thereof.

DETAILED DESCRIPTION OF THE INVENTION

The term "amino group" as used herein for the $R_2$ moiety means a primary amino group having the formula $-NH_2$.

The term "halogen atom" as used herein includes fluorine, chlorine, bromine and iodine atoms.

The term "alkyl group" as used herein means a straight or branched chain alkyl group having 1 to 4 carbon atoms such as a methyl, ethyl, propyl, isopropyl, butyl, isobutyl, sec-butyl, and tert-butyl group.

The term "alkoxy group" as used herein means an alkoxy group having 1 to 4 carbon atoms such as a methoxy, ethoxy, propoxy, isopropoxy, butoxy, isobutoxy, sec-butoxy and tert-butoxy group.

The

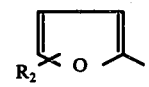

group used for the X moiety designates groups such as a 2-furyl, 4-nitro-2-furyl, 5-nitro-2-furyl, 5-amino-2-furyl, 5-chloro-2-furyl, 3-bromo-2-furyl, 4-bromo-2-furyl, 5-bromo-2-furyl, 3-iodo-2-furyl, 5-iodo-2-furyl, 5-methyl-2-furyl, 5-ethyl-2-furyl, 5-propyl-2-furyl, 5-butyl-2-furyl, 5-isobutyl-2-furyl, 5-methoxy-2-furyl, 5-hydroxy-2-furyl group, etc The

group used for the X moiety designates groups such as a 2-thienyl, 4-nitro-2-thienyl, 5-nitro-2-thienyl, 5-amino-2-thienyl, 3-hydroxy-2-thienyl, 3-chloro-2-thienyl, 5-chloro-2-thienyl, 3-bromo-2-thienyl, 4-bromo-2-thienyl, 5-bromo-2-thienyl, 4-iodo-2-thienyl, 5-iodo-2-thienyl, 3-fluoro-2-thienyl, 5-fluoro-2-thienyl, 3-methyl-2-thienyl, 5-methyl-2-thienyl, 5-ethyl-2-thienyl, 5-propyl-2-thienyl, 5-butyl-2-thienyl, 5-isobutyl-2-thienyl, 3-methoxy-2-thienyl, 5-methoxy-2-thienyl, 5-ethoxy-2-thienyl, 5-propoxy-2-thienyl, 5-butoxy-2-thienyl group, etc.

The pharmaceutically acceptable salts include, for example, salts of alkali metals such as lithium, sodium and potassium, alkaline earth metals as calcium and barium and ammonia and the like.

A preferred class of (E)-2-[p-(β-substituted-vinyl)-phenyl]alkanoic acids of the formula (I) above is those compounds where $R_1$ represents a hydrogen atom or a methyl group; and X represents a

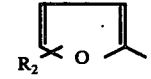

group, wherein $R_2$ represents a hydrogen atom, a nitro group, an amino group, a halogen atom, a methoxy group, or an alkyl group having 1 to 4 carbon atoms, with $R_2$ preferably representing a hydrogen atom, a nitro group, a chlorine atom, a methyl group or an isopropyl group.

Another preferred class of (E)-2-(β-substituted-vinyl)phenyl]alkanoic acids of the formula (I) above is those compounds wherein $R_1$ represents a hydrogen atom or a methyl group; and X represents a

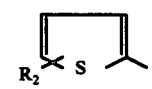

group, wherein $R_2$ represents a hydrogen atom, a fluorine atom, a chlorine atom, a bromine atom, an amino group, a methyl group, an ethyl group or a methoxy group, with $R_2$ preferably representing a hydrogen atom, an amino group, a fluorine arm, a chlorine atom or a methoxy group.

Specific preferred examples of the compounds of the formula (I) above include (E)-2-[p-($\beta$-2-furylvinyl)-phenyl]propionic acid, (E)-2-[p-($\beta$-thienylvinyl)-phenyl]propionic acid, (E)-p-($\beta$-2-thienylvinyl)-phenylacetic acid, (E)-2-[p-($\beta$-5-chloro-2-thienylvinyl)-phenyl]propionic acid, (E)-p-($\beta$-5-chloro-2-thienyl-vinyl)phenylacetic acid, and the pharmaceutically acceptable salts thereof.

As is apparent to one skilled in the art, the compounds of the present invention having the formula (I) exist in stereoisomeric forms with respect to the groups connected to the vinyl group as shown below:

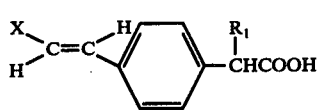

(I)

wherein X and $R_1$ are as defined previously. In the compounds of the formula (I), the substituent X and the phenylalkanoic acid moiety are connected to the vinyl group on opposite sides with respect to the C=C bond plane, and the compounds are designated as (E)-type compounds (i.e., "entgegen"). However, for simplicity, the vinyl moiety of the compounds disclosed herein (i.e., compounds of the formulae (I), (Ia), (Ib), (II), (IIa), (III), (IV), (V) and (VI)) is described hereinafter as X—CH=CH—.

The (E)-2-[p-($\beta$-substituted-vinyl)phenyl]alkanoic acids of this invention represented by the formula (I) can be prepared by either one of the two alternative procedures as schematically illustrated below:

PROCESS I
Step Reaction Scheme

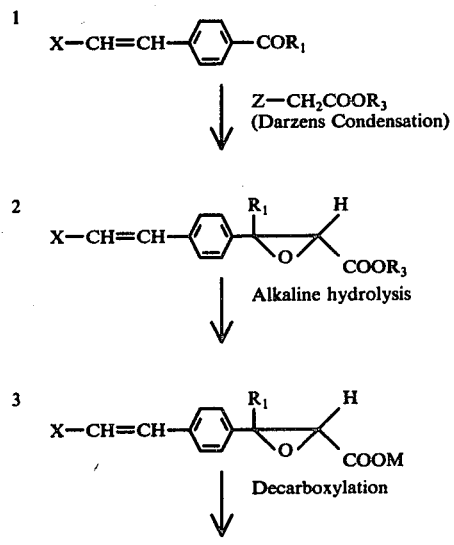

PROCESS I
Step Reaction Scheme

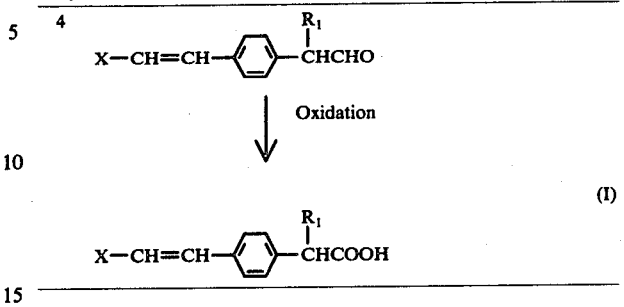

wherein $R_1$ and X are as defined above; $R_3$ represents an alkyl group having 1 to 7 carbon atoms; Z represents a chlorine, bromine or iodine atom; and M represents an alkali metal atom or a ½ alkaline earth metal atom.

PROCESS II
Step Reaction Scheme

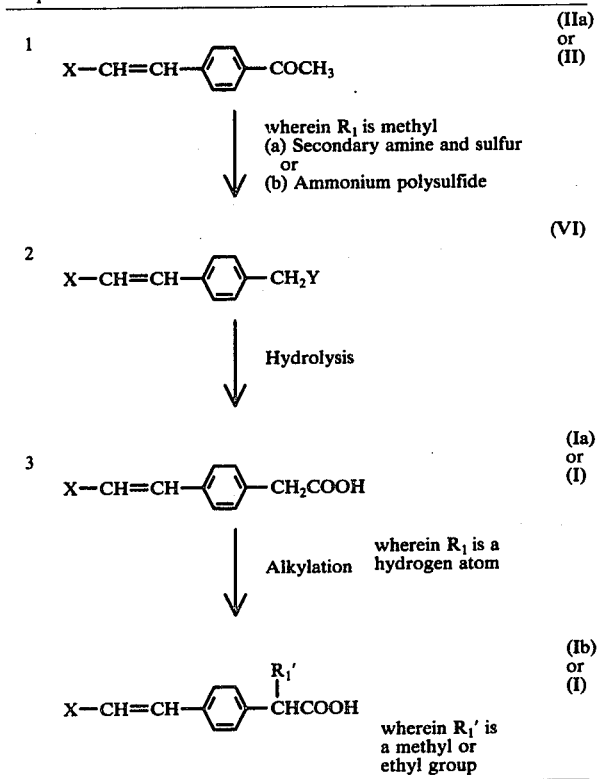

wherein X is as defined above; Y represents

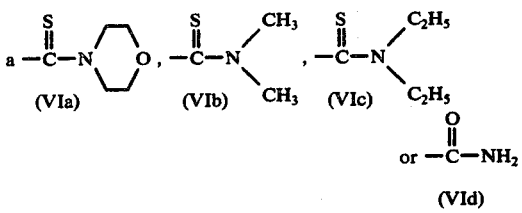

group; and $R_1'$ represents a methyl or ethyl group.

The compounds of the formulae (III), (IV), (V) and (VI) described above are also novel and are useful as intermediates in preparing the compounds of the formula (I) of this invention.

The starting materials, (E)-4-acyl-β-substituted-styrene of the formula (II) used in the above Process I and Process II can easily be obtained by the process as disclosed in Japanese Pat. Application No. 77781/1974. That is, a β-substituted-acrylic acid is reacted with a diazonium salt in the presence of a copper salt, such as cupric chloride, as a catalyst to obtain the desired (E)-4-acyl-β-substituted-styrene of the formula (II). The preparation of the starting material of the formula (II) will be described in greater detail in the Reference Examples hereinafter given.

Process I of the present invention comprises the following 4 steps.

STEP 1

An (E)-4-acyl-β-substituted-styrene of the formula (II) obtained as above is reacted with an α-haloacetic acid ester to obtain a glycidic acid ester of the formula (III). Suitable alkyl groups having 1 to 7 carbon atoms used for the $R_3$ moiety of the α-haloacetic acid ester include, for example, methyl, ethyl, propyl, iso-propyl, butyl, iso-butyl, pentyl, hexyl, heptyl groups, etc., preferably a lower alkyl having 1 to 4 carbon atoms, and most preferably an ethyl group.

The reaction can be carried out under an inert atmosphere, such as nitrogen gas, and in a solvent under anhydrous conditions in the presence of an alkali condensing agent (Darzens condensation). Examples of alkalis which can be used in this reaction as a condensing agent are sodium amide, potassium amide, sodium hydroxide, sodium methoxide, sodium iso-propoxide, potassium t-butoxide, lithium diethylamide and the like. Examples of solvents which can be used in the above reaction include, for example, alkanols, e.g., methanol, ethanol, iso-propanol, butanol, etc., ethers, e.g., diethyl ether, hydrocarbons such as toluene, xylene, etc., and light oil. Of these condensing agents and solvents, a combination of sodium iso-propoxide with iso-propanol or a combination of potassium t-butoxide with t-butanol is preferably employed. The reaction between the (E)-4-acyl-β-substituted-styrene of the formula (II) and the α-haloacetic acid ester can be conducted using about 1 to 2.5 moles, preferably 1.8 to 2.0 mols, of the α-haloacetic acid ester per mole of the (E)-4-acyl-β-substituted-styrene of the formula (II). The reaction temperature can be varied within the range of from about 0° C to the refluxing temperature of the system, and the optimum temperature will depend upon the condensing agent and the solvent employed. A preferred temperature range is from 0° C to room temperature (about 20°to 30° C).

When the alkyl group designated by the $R_3$ moiety of the α-haloacetic acid ester is the same as the alkyl moiety of the alkanol used for the preparation of the alkoxide condensing agent, the reaction product can be isolated as a sufficiently pure compound.

STEP 2

The glycidic acid ester of the formula (III) as obtained in Step 1 is hydrolyzed in the presence of an alkali to form a glycidic acid salt of the formula (IV). Examples of alkalis which can be used in this reaction can include alkali metal hydroxides such as sodium hydroxide, potassium hydroxide and the like and alkaline earth metal hydroxides such as calcium hydroxide, barium and the like. The resulting sodium, potassium and calcium salts are typical hydrolysis products of esters, and isolation thereof by salting-out from an aqueous solution can be carried out by precipitation from an alkanolic aqueous solution.

STEP 3

The thus-isolated glycidic acid salt of the formula (IV) is refluxed by heating at a temperature of from about 90° to 140° C, preferably 110° to 120° C, for a period of from about 3 to 6 hours, preferably 3 to 4 hours, in an aqueous solution at a pH of about 6 to 8, preferably 7 to 8, under an inert atmosphere, such as $N_2$ gas, to effect decarboxylation and ring opening thereby obtaining an aldehyde compound of the formula (V).

STEP 4

The aldehyde compound of the formula (V) as obtained in Step 3 is oxidized using (1) about 2 to 2.5 moles, preferably about 2 moles, of an oxidizing agent per moles of the aldehyde compound of the formula (V), such as potassium permanganate, hydrogen peroxide, nitric acid, chromic anhydride, silver oxide, etc., or (2) an equimolar amount of oxygen gas in the presence of a small amount of cobalt acetate catalyst; and the like. Among these oxidizing agents, silver oxide is particularly preferred. Examples of solvents which can be used in the above reaction include a mixed solvent of water and an alkanol such as methanol, ethanol, propanol, iso-propanol or the like, preferably a mixed solvent of ethanol with water or methanol with water. When the aldehyde compound of the formula (V) is sparingly soluble in the above enumerated solvent, tetrahydrofuran, dioxane and the like can be appropriately added to the solvent system.

In carrying out the oxidation, an alkali, for example, an aqueous solution of sodium hydroxide, is added dropwise to a mixture of the aldehyde compound of the formula (V), silver oxide and a water-ethanol mixed solvent, and the resulting mixture is stirred at room temperature (about 20° to 30° C) for about 2 to 3 hours. The silver oxide is then filtered out, and the filtrate is distilled to remove the volatile solvent used, i.e., ethanol in this instance. The residue is washed with a solvent which is immiscible with water such as diethyl ether, benzene and the like. The aqueous layer of the resulting mixture is made acidic, e.g., with hydrochloric acid and then extracted with an appropriate solvent such as diethyl ether, petroleum ether, n-hexane, ethyl acetate, a combination of two of these solvents and the like. The extract is evaporated to dryness, and the residue is purified by crystallization from light oil or the like to obtain the desired compound of the formula (I).

Process II comprises the following 3 steps.

STEP 1

The secondary amines which can be used in this step include dialkylamines such as dimethylamine or diethylamine, and morpholine. Morpholine is particularly preferred since it permits the reaction to be operated in an open vessel. In a preferred embodiment, morpholine and sulfur are added to the starting material, (E)-p-(β-substituted-vinyl) acetophenone, of the formula (IIa) followed by heating in a stream or oil bath at atmospheric pressure to obtain a carbothiomorpholide of the formula (IVa). The reaction can be carried out in the absence of a solvent, but, if desired, a solvent such as pyridine, dioxane and the like may be optionally employed. Morpholine amine can be used in an amount of about 2 to 5 moles, preferably 2 to 2.5 moles, per mole of the (E)-4-p-(β-substituted-vinyl)-acetophenone of the formula (IIa), and the sulfur can be used in an amount of about 2 to 3, preferably 2 to 2.5 moles, per mole of the (E)-p-(β-substituted-vinyl) acetophenone of the formula (IIa). The reaction temperature can range from about 80° C to 150° C, preferably, at the refluxing temperature of the reaction system. The reaction time ranges from about 3 to 24, preferably 3 to 4, hours. The reaction can also be conducted using dimethylamine, diethylamine and the like in place of morpholine in a closed vessel by heating at a temperature of from about 180° C to 200° C for about 12 to 24 hours to obtain a carbothioamide of the formula (IVb) or (VIc).

Alternatively, the above reaction can be effected using about 1.8 to 2.0 moles of an ammonium polysulfide per mole of the starting material, (E)-p-(β-substituted-vinyl)-acetophenone, of the formula (II) instead of the secondary amine and sulfur in a solvent such as dioxane, ethanol, pyridine and the like. In this case, the reaction mixture is heated in a closed vessel at a temperature of from about 200° to 250° C for a period of from about 5 to 24 hours to obtain a carboxamide of the formula (IVd).

The thus-obtained carboxamide of the formula (IVd), or carbothioamide of the formula (VIa), (VIb) or (VIc) can be subjected to the subsequent hydrolysis step either with or without isolation.

STEP 2

The carbothioamide of the formula (IVa), (VIb) or (VIc) is hydrolyzed by adding a strong acid, such as hydrochloric acid and the like, or a strong base, such as sodium hydroxide, potassium hydroxide and the like, to the reaction mixture obtained in Step 1 above. When the carbothioamide of the formula (VIa), (VIb) or (VIc) has been isolated from the reaction mixture in Step 1, the hydrolysis can be carried out by dissolving the carbothioamide in a solvent such as acetic acid, dioxane and the like. When an acid is used for the hydrolysis, after the reaction, the acetic acid, dioxane or the like is distilled off under reduced pressure, and the residue is concentrated followed by extraction with a water-immiscible solvent, for example, an organic solvent, such as diethyl ether, benzene, chloroform, dichloromethane, petroleum ether and the like, to isolate the reaction product. When a base is employed for the hydrolysis, the cooled reaction mixture is made acidic with hydrochloric acid and the like. The thus-formed precipitate or oily substance is then filtered or extracted with the above enumerated waterimmiscible solvent to isolate the reaction product.

The hydrolysis of the carboxamide of the formula (VId) can be carried out by refluxing the carboxamide of the formula (VId) together with the above-described strong base dissolved in an alcoholic aqueous solution, such as an aqueous methanolic and ethanolic solution. After completion of the hydrolysis, the alcohol used is distilled off, and the residue is concentrated. The concentrate is then poured into ice-cooled hydrochloric acid thereby precipitating a free acid of the formula (Ia), which is then purified and isolated.

The reaction time for the hydrolysis of the carbothioamide or carboxamide of the formulae (IVa), (VIb), (VIc) and (VId) generally ranges from about 10 to 24 hours, using about 2 to 10 moles, preferably 4 to 5 moles, of the acid or base per mole of the carbothioamide or the carboxamide.

STEP 3

The phenylacetic acid derivative of the formula (Ia) obtained in Step 2 is an (E)-p-(β-substituted-vinyl) phenylacetic acid which is represented by the formula (I) wherein $R_1$ is a hydrogen atom. The desired compounds of the formula (Ib) (the compounds of the formula (I) wherein $R_1'$ represents a methyl group or an ethyl group) can be prepared by reacting the phenylacetic acid of the formula (Ia) with an alkyl halide in the presence of a base either as it is isolated in Step 2 or after converting the carboxylic acid group thereof into a nitrile, an amide, a lower alkyl ester and the like as illustrated in the following reaction scheme.

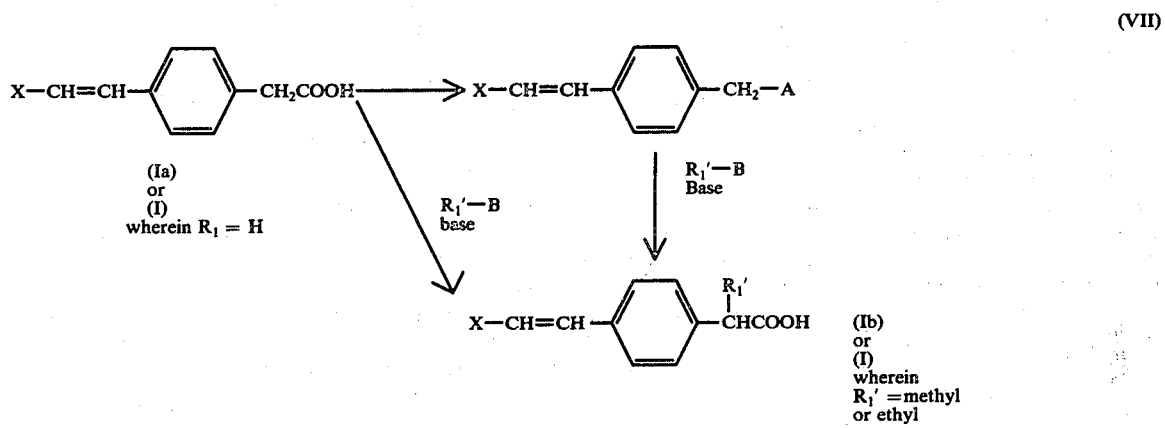

(VII)

wherein X is as defined above, A represents a —CN, —CONH$_2$ or —COOR$_4$ group in which $R_4$ represents a methyl, ethyl, propyl, isopropyl, butyl, isobutyl, sec-butyl or tert-butyl group, $R_1$ represents a methyl or ethyl group and B represents a bromine or iodine atom.

As is described previously, the (E)-2-[p-(β-substituted-vinyl)phenyl]alkanoic acids of the formula (I) possess anti-inflammatory, analgesic, antipyretic and platelet aggregation inhibitory activities. These pharmacological activities of the compounds of the present invention were determined as follows:

The anti-inflammatory activity of the compounds against carrageenin-induced edema was determined according to procedure described in C.A. Winter et al., Proc. Soc. Exp. Biol. Med., 111, 544 (1962). Male Wistar rats, each weighing 100 to 120 g were used. Hind paw edema was induced by sub-cutaneous injection of 0.1 ml of 1% carrageenin solution into the left foot pad of each rat. Hind paw volume was measured before and after challenge of carrageenin by immersion of the hind paw down to the lateral malleolus into a glass cylinder containing water. Each dose of the test compound was orally administered one hour before challenge of carrageenin.

$ED_{50}$-value was calculated from the number of positive animals showing an inhibitory activity of b 25% or more than the matched control group at 3 hours after carrageenin challenge.

An example of the strong anti-inflammatory activity revealed by the present invention is shown in Table I.

TABLE I

Anti-inflammatory activity of (E)-2-[p-($\beta$-2-thienylvinyl)phenyl]-propionic acid (XG-28; present invention) together with 2-(p-isobutylphenyl)propionic acid (ibuprofen) in rats by the method of carrageenin-induced hind paw edema

| Dose (mg/kg p.o.) | n | ( )a) | Hind Paw Swelling and Percent Inhibition | | | |
|---|---|---|---|---|---|---|
| | | | 2 Hours | | 3 Hours | |
| | | | Swelling (%) Mean ± S.E. | (%) | Swelling (%) Mean ± S.E. | (%) |
| Control Vehicle | 8 | (0) | 75.6 ± 3.1 | | 73.2 ± 2.8 | |
| XG-28    1 | 5 | (0) | 73.7 ± 3.7 | 2.4 | 73.9 ± 2.6 | −1.0 |
|          2.5 | 5 | (0) | 67.0 ± 2.6 | 11.3 | 70.12 ± 2.1 | 4.0 |
| Control Vehicle | 16 | (0) | 75.5 ± 1.7 | | 73.1 ± 1.8 | |
| XG-28    5 | 10 | (1) | 62.9 ± 3.2** | 16.8 | 68.2 ± 2.7 | 6.7 |
|          10 | 10 | (0) | 60.5 ± 2.3** | 19.8 | 65.7 ± 2.0* | 10.1 |
| Control Vehicle | 16 | (0) | 76.4 ± 1.3 | | 74.8 ± 1.7 | |
| XG-28    20 | 10 | (6) | 50.7 ± 3.7** | 33.6 | 56.0 ± 4.1** | 25.2 |
| Control Vehicle | 16 | (0) | 76.4 ± 1.7 | | 74.9 ± 1.9 | |
| XG-28    40 | 10 | (8) | 46.8 ± 2.6** | 38.7 | 48.6 ± 3.1** | 35.1 |
| Control Vehicle | 16 | (0) | 72.4 ± 2.1 | | 71.4 ± 2.0 | |
| XG-28    80 | 9 | (7) | 49.8 ± 2.6** | 31.3 | 49.3 ± 2.8** | 30.9 |
| $ED_{50}$ (XG-28) = 23.3 (13.8 − 39.5) mg/kg, p.o.:n = 54 | | | | | | |
| Control Vehicle | 10 | (0) | 66.5 ± 4.4 | | 72.0 ± 2.8 | |
| Ibuprofen 10 | 5 | (1) | 57.4 ± 3.9* | 13.6 | 60.8 ± 4.7* | 15.5 |
|          20 | 10 | (4) | 52.6 ± 3.4* | 20.9 | 56.2 ± 2.7** | 21.9 |
|          40 | 10 | (7) | 47.5 ± 4.0** | 28.6 | 51.2 ± 4.0** | 28.9 |
|          80 | 10 | (9) | 41.8 ± 2.3** | 37.2 | 43.9 ± 2.4** | 38.9 |
| $ED_{50}$ (ibuprofen) = 24.3 (10.6 − 39.2) mg/kg, p.o.:n = 35 | | | | | | |

*0.01 < P < 0.05
**P < 0.01 different from each control group
a)number of positive rats Analgesic activity was determined according to the Phenylquinone-Writhing Syndrome method. ddN strain mice, each weighing about 18 to 22 g were used. Chemical pain was induced by an intraperitoneal injection of 0.1 ml/10 g body weight of 0.03% phenylquinone in 5% aqueous ethanol into the mice. The number of writhings was measured for 15 minutes from 5 minutes after challenge of phenylquinone. Each dose of the drug was given 30 minutes before challenge of phenylquinone.

$Ed_{50}$-value was calculated from the number of positive animals showing fewer writhings than half of the matched control group.

An example of the strong analgesic activity revealed by the present invention is shown in Table II.

TABLE II

Analgesic activity of (E)-2-[p-($\beta$-2-thienylvinyl)phenyl]-propionic acid (XG-28, present invention) together with 2-(p-isobutylphenyl)propionic acid (ibuprofen) in mice by the Phenylquinone-Writhing Syndrome Method.

| Dose (mg/kg p.o.) | n | ( )a) | Number of Writhings/15 min. | |
|---|---|---|---|---|
| | | | Mean ± S.E. | Inhibition in (%) |
| Control Vehicle | 23 | ( 0) | 19.4 ± 0.8 | |
| XG-28    0.5 | 6 | ( 1) | 16.8 ± 2.1 | 13.5 |
|          5 | 5 | ( 2) | 14.4 ± 6.0 | 25.8 |
|          10 | 6 | ( 2) | 13.7 ± 2.4** | 29.4 |
|          25 | 10 | ( 7) | 5.6 ± 1.8** | 71.1 |
|          50 | 10 | ( 4) | 9.3 ± 1.6** | 52.1 |
|          100 | 10 | ( 9) | 7.0 ± 2.0** | 63.9 |
|          200 | 6 | ( 5) | 7.7 ± 1.2** | 60.3 |
| $ED_{50}$ (XG-28) = 14.1 (4.31 − 46.2) mg/kg, p.o.:n = 53 | | | | |
| Control Vehicle | 22 | ( 0) | 36.8 ± 1.3 | |
| Ibuprofen 25 | 7 | ( 2) | 27.4 ± 3.3* | 25.5 |
|          50 | 10 | ( 4) | 20.0 ± 1.5** | 45.7 |
|          100 | 10 | ( 8) | 13.1 ± 1.9** | 64.4 |
|          200 | 10 | (10) | 8.7 ± 1.6** | 76.4 |
|          400 | 10 | (10) | 1.9 ± 0.8** | 94.8 |

TABLE II-continued

Analgesic activity of (E)-2-[p-($\beta$-2-thienylvinyl)phenyl]-propionic acid (XG-28, present invention) together with 2-(p-isobutylphenyl)propionic acid (ibuprofen) in mice by the Phenylquinone-Writhing Syndrome Method.

| Dose (mg/kg p.o.) | n | ( )a) | Number of Writhings/15 min. | |
|---|---|---|---|---|
| | | | Mean ± S.E. | Inhibition in (%) |
| $ED_{50}$ (ibuprofen) = 50.0 (32.7 − 76.2) mg/kg, p.o.:n = 37 | | | | |

*0.01 < P < 0.05
**P < 0.01 different from each vehicle control group
a)number of positive mice The antipyretic activity of the compounds of this invention was determined as follows. Male rats, weighing about 160 to 170 g, received an intravenous injection of a beer yeast. Those animals which showed an elevation in body temperature by more than 1 degree C within 1 to 1.5 hours after the injection were chosen and divided into groups, each containing 8 rats. The test compound was intraperitoneally administered to each of the rats, and thereafter the body temperature of each rat was determined for a period of 3.5 hours. The results obtained indicated that the compound of the present invention exhibited an antipyretic activity about 10 to 20 times that exhibited by aspirin.

The platelet aggregation inhibitory activity of representative compounds of the formula (I) were determined in terms of the present inhibitory activity against collagen-induced platelet aggregation in rabbit platelet-rich plasma according to the procedure described by G.V.R. Born and M.J. Cross in *Journal of Physiology*, Vol. 168, p. 178 (1963). The activity was evaluated after a 3 minute incubation of a mixture of the platelet aggregation inhibitor and rabbit platelet-rich plasma. The inhibition percentages are not absolute since the sensitivity of platelets to aggregating agents varied from preparation to preparation. Accordingly, the relative potency of inhibition of the test compound to aspirin ($R_{ASP}$) at the same concentration was chosen as a direct measure of inhibition potency. Table III reveals that compounds of the present invention show strong platelet aggregation inhibitory activity.

TABLE III

Inhibition of Collagen Induced Platelet Aggregation

| Compound | Solvent | Concentration (M) | $R_{ASP}$ |
|---|---|---|---|
| Aspirin | 0.02N NaOH | $10^{-4}$ | 1.0 |
| (E)-4-(β-Thienylvinyl)phenylacetic acid (present invention) | " | " | 1.0 |
| (E)-2-[4-(β-Thienylvinyl)phenyl]propionic acid (present invention) | " | " | 1.6 |
| p-Isobutylphenylacetic acid | " | " | 0.5 |
| 2-(p-Isobutylphenyl)propionic acid | " | " | 0.6 |

In addition, the (E)-2-[p-(β-substituted-vinyl)phenyl]alkanoic acids of the formula (I) according to the present invention have a low toxicity when orally administered to mice.

The (E)-2-[p-(β-substituted-vinyl)phenyl]alkanoic acids of the formula (I) can be administered to humans via oral, rectal and parenteral routes, preferably via oral and rectal routes. The dose level can be appropriately selected according to the administration route, the purpose of the administration and the like, but generally these compounds can be administered via non-parenteral routes at a dose level of about 1 to 30 mg/kg body weight per day to an adult, in single or multiple doses.

The compounds of this invention can be administered alone or in combination with conventional pharmaceutical excipients, disintegrating agents, binders, lubricants, solubilizing agents, emulsifying agents, suspending agents, stabilizers, buffering agents, isotonic agents, preservatives, etc., in dosage forms such as powders, tablets, capsules, syrups, granules, pills, suppositories, liquids, emulsions, injectable solutions, and the like which are well known in the art.

The present invention is further illustrated by the following Reference Examples and Examples, which are given for illustrative purposes only and are not to be construed as limiting the invention. Unless otherwise indicated, all parts, percents, ratios and the like are by weight.

REFERENCE EXAMPLE 1

Preparation of (E)-2-(4-Acetylstyryl)thiophene of the Formula (II) wherein X is a 2-thienyl group and $R_1$ is a methyl group 9.3 g of sodium nitrite dissolved in the minimum amount of water was added to a mixture of 18.18 g of p-amino-acetophenone, 36 ml of concentrated hydrochloric acid and 36 g of water, and the resulting mixture was ice-cooled and diazotized while stirring. To the diazotized solution was added 127 cc of a solution of 16.9 g of β-2-thienylacrylic acid in acetone. An aqueous solution of 25.4 g of sodium acetate dissolved in 10 ml of water and 5.6 g of cupric chloride were then added to the mixture whereby a gas evolved and the reaction proceeded. After the reaction mixture was stirred for 24 hours while cooling, the acetone was distilled off and the residue was extracted with benzene. The benzene layer was shaken with a 5% aqueous sodium hydroxide solution, washed with water and dried over $Na_2SO_4$. The drying agent used was filtered out and the solvent was distilled off. The resulting residue was purified by column chromatography on alumina using benzene as a developing solvent to obtain 13.73 g of (E)-2-(4-acetylstyryl)thiophene in a 50% yield. The melting point of the product after recrystallization from benzene was 130° to 131° C.

IR Absorption Spectrum $\nu$ cm$^{-1}$: 1670 (CO)
NMR Spectrum (CDCl$_3$) δ:
  2.56 (singlet, 3H, CH$_3$),
  6.8 - 7.4 (multiplet, 5H, olefin and thiophene-H),
  7.5 (doublet, 2H, J = 8Hz aromatic H) and
  7.9 (doublet, 2H, J = 8Hz, aromatic H)
Elemental Analysis:
  Calcd. for C$_{14}$H$_{12}$OS (%): C 73.65, H 5.30.
  Found (%) C 73.41, H 5.22.

REFERENCE EXAMPLE 2

Preparation of (E)-2-(4-Acetylstyryl) furan of the formula (II) wherein X is a 2-furyl group and $R_1$ is a methyl group In the same manner as described in Reference Example 1 but using 20 g of β-2-furylacrylic acid in place of the β-2-thienylacrylic acid, 18.43 g (60% yield) of (E)-2-(4-acetylstyryl)furan was obtained. The product thus-obtained had the following characteristics.

Melting Point: 146° C (after recrystallized from benzene)
IR Absorption Spectrum $\nu$ cm$^{-1}$: 1680 (CO)
NMR Spectrum (CDCl$_3$) δ:
  2.56 (singlet, 3H, CH$_3$),
  6.36 - 8.16 (multiplet, 9H, olefin, aromatic H)

REFERENCE EXAMPLE 3

Preparation of (E)-2-(4-Acetylstyryl)-5-chlorothiophene

To a solution of 3.57 g of p-aminoacetophenone and 7.15 ml of concentrated hydrochloric acid in 7.15 ml of water was added an aqueous solution of 1.82 g of NaNO$_2$ dissolved in a minimum amount of water while cooling with ice and stirring to effect a diazotization reaction. Then, to the resulting mixture were added a solution of 5.0 g of β-(5-chloro)-2-thienylacrylic acid dissolved in 25 ml of dimethyl sulfoxide slowly and thereafter a solution of 1.10 g of cupric chloride and 5.0 g of sodium acetate dissolved in a minimum amount of water. The mixture was then stirred for 3 hours while cooling followed by stirring at room temperature for 24 hours. After completion of the reaction, the reaction mixture was poured into a large amount of water to precipitate crystals which were then filtered and dissolved in benzene. The resulting solution was thoroughly washed with 5% aqueous solution of sodium hydroxide and water, and the benzene layer was dried over anhydrous magnesium sulfate. The benzene was distilled off to obtain crude crystals. Recrystallization from a mixture of benzene and n-hexane (1:1) by volume) yielded 1.6 g (30% yield) of the product as a light brown powder having a melting point of 115° C and the following characteristics:

IR Absorption Spectrum ($\nu$KRr/max cm$^{-1}$): 1670 (C=O)
NMR Spectrum (CDCl$_3$) δ:
  2.56 (s, 3H, CH$_3$CO—),
  6.56 - 7.33 (m, 4H, thiophene 2H + olefin 2H),
  7.43 (d, 2H, J = 8 cps, aromatic 2H),
  7.93 (d, J = 8 cps, 2H, aromatic 2)
Elemental Analysis:
  Calcd. for C$_{14}$H$_{11}$OClS: C 63.99; H 4.22.
  Found: C 64.47; H 4.23.

EXAMPLE 1

Preparation of
(E)-2-[p-(β-2-Furylvinyl)phenyl]propionic Acid a. Ethyl (E)-3-[p-(β-2-Furylvinyl)phenyl]-2,3-epoxybutyrate 3 g of (E)-2-(4-acetylstyryl)furan prepared in Reference Example 2 and 3.12 of ethyl chloroacetate were dissolved in dried benzene. A t-butanol solution of potassium t-butoxide prepared from 0.94 g of potassium metal and 30 ml of t-butanol was added dropwise to the above solution under a nitrogen atmosphere while water-cooling and stirring over a period of 1.5 hours. After the stirring was further continued for additional two hours in ice-water, the reaction mixture was refluxed for 2 to 3 hours followed by distillation under reduced pressure to remove the t-butanol. Water was added to the residue and the aqueous solution was extracted with diethyl ether and dried over $NA_2SO_4$. After distillation of the diethyl ether, the reaction product was recrystallized from ethanol to obtain the above-titled compound in an 80% yield. Since this compound does not crystallize, it was used in the subsequent reaction step after chromatography on a silica gel column.

IR Absorpiton Spectrum $\nu$ cm$^{-1}$: 1740 (ester)

b. Sodium (E)-3-[p-(β-2-Furylvinyl)phenyl]-2,3-epoxybutyrate 2.35 g of the ethyl (E)-3- [p-(β-2-furylvinyl)phenyl]-2,3-epoxybutyrate obtained in (a) above was dissolved in 45 ml of ethanol, and to the resulting solution was added an ethanolic solution of sodium ethoxide prepared from 0.15 g of sodium metal and 20 ml of absolute ethanol at room temperature while stirring. 0.12 ml of water was then added thereto, and the mixture was further stirred for 24 hours to obtain 2.15 g of sodium (E)-3-[p-(β-2-furylvinyl)phenyl]-2,3-epoxybutyrate in a 93% yield.

IR Absorpiton Spectrum $\nu$ cm$^{-1}$: 1600 (—COONa).

c. (E)-2-[p-(β-2-Furyl inyl)phenyl]propanal 2.15 g of the sodium (E)-3-[p-(β-2-furylyvinyl)-phenyl]-2,3-epoxybutyrate obtained in (b) above as suspended in 60 ml of water, and 0.3 ml of concentrated hydrochloric acid was added to the suspension. The resulting mixture was refluxed at a temperature of 110° to 130° C for 3 hours while purging the system with nitrogen gas. The reaction mixture was cooled to precipitate the product, which was then extracted with diethyl ether and dried over $Na_2SO_4$ to obtain 1 g of the above-titled compound having a melting point of 60° to 61° C (recrystallized from n-hexane) in a 60% yield.

IR Absorption Spectrum $\nu$ cm$^{-1}$: 1710 (CHO)

NMR Spectrum (CDCl$_3$) δ:
1.46 (doublet, 3H, J = 8Hz, CH$_3$),
3.6 (quartet, 1H, J = 8Hz,

6.4 (multiplet, 2H, olefin),
7.0 - 7.6 (multiplet, 7H, aromatic H) and
9.63 (singlet, 1H, -CHO).

d. (E)-2-[p-(β-2-Furylvinyl)phenyl]propionic Acid 0.5 g of the (E)-2-[p-(β-2-furylvinyl)phenyl]propanal obtained in (c) above was dissolved in 7 cc of ethanol, and to the resulting solution was added an aqueous solution of 0.74 g of silver nitrate dissolved in 20 ml of water. An aqueous solution of 0.5 g of sodium hydroxide in 20 ml of water was then added dropwise to the above solution followed by stirring at room temperature for 2 hours. The silver oxide was separated by filtration and the filtrate was distilled to remove the ethanol. The aqueous layer was extracted with diethyl ether, and the separated aqueous layer was made acidic with concentrated hydrochloric acid, extracted with diethyl ether and dried over MgSO$_4$ to obtain 0.42 g (80% yield) of the above-titled product, i.e., (E)-2-[p-(β-2-furylvinyl)phenyl]propionic acid, having a melting point of 126° C (recrystallized from n-hexane-chloroform, 1 : 1 by volume).

IR Absorption Spectrum $\nu$ KBr/cm$^{-1}$:
3000 - 2500 (—COOH)
1700 (—COOH)

NMR Spectrum (CDCl$_3$) δ:
1.5 (doublet, 3H, J = 8Hz, CH$_3$),
3.7 (quartet, 1H, J = 8Hz,

6.33 (singlet, 2H, olefin H),
6.9 (multiplet, 2H, furan H) and
7.2 - 7.6 (multiplet, 5H, furan + aromatic H)

In the same manner as described in Example 1, each of the following compounds of the formula (I) can also be produced from each of the starting materials of the formula (II).

| Starting Material of Formula (II) | Compound of Formula (I) |
|---|---|
| (E)-2-(4-Acetylstyryl)-5-chlorofuran | (E)-2-p-[β-(5-Chloro-2-furyl)vinyl]phenylpropionic acid |
| (E)-2-(4-Acetylstyryl)-5-nitrofuran | (E)-2-p-[β-(5-Nitro-2-furyl)vinyl]phenylpropionic acid |
| (E)-2-(4-Acetylstyryl)-5-isopropylfuran | (E)-2-p-[β-(5-Isopropyl-2-furyl)vinyl]phenylpropionic acid |
| (E)-2-(4-Acetylstyryl)-5-methylfuran | (E)-2-p-[β-(5-Methyl-2-furyl)vinyl]phenylpropionic acid |

EXAMPLE 2

Preparation of
(E)-2-[p-(β-2-Thienylvinyl)phenyl]propionic Acid a. Ethyl (E)-3-[p-(β-2-Thienylvinyl)phenyl]-2,3-epoxybutyrate 1.25 g of (E)-2-(4-acetylstyryl)thiophene and 1.35 g of ethyl monochloroacetate were dissolved in 40 ml of dried benzene. Potassium t-butoxide prepared from 0.43 g of potassium metal and 20 ml of t-butanol was added dropwise to the above solution at room temperature over a period of 1 hour while purging the system with nitrogen gas. After allowing the mixture to react for 24 hours, the t-butanol was distilled off, and the residue was poured into ice-water, and extracted with diethyl ether. The extract was washed with water and then dried over Na$_2$SO$_4$ to obtain 1.6 g of crude ethyl (E)-3-[p-(β-2-thienylvinyl)phenyl]-2,3-epoxybutyrate. Since this compound does not crystallize, it was subjected to the subsequent reaction step after chromatographing using a silica gel column.

IR Absorption Spectrum $\nu$ cm$^{-1}$: 1740 (ester).

b. Sodium (E) -3-[p-(β-2-Thienylvinyl)phenyl]-2,3-epoxybutyrate 1.6 g of the crude ethyl (E)-3-[p-(β-2-thienylvinyl)-phenyl]-2,3-epoxybutyrate obtained in (a) above was dissolved in 50 cc of distilled ethanol, and sodium ethoxide prepared from 116 mg of metallic sodium and 10 cc of distilled ethanol was added to the resulting solution all at once. 5 drops of water were then added thereto using a pipette followed by stirring at room temperature for 24 hours. The yellowish white precipitate thus formed was filtered and washed successively with ethanol and diethyl ketone to obtain 0.65 g of the above-titled compound as a yellowish white powder.
IR Absorption Spectrum ν cm⁻¹: 1600 (—COONa)

c. (E)-2-[p-(β-2-Thienylvinyl)phenyl]propanal 0.57 g of the sodium (E)-3-[p-(β-2-thienylvinyl)-phenyl]-2,3-epoxybutyrate obtained in (b) above was suspended in 10 cc of water, and dilute hydrochloric acid was added dropwise to the suspension to adjust the pH to about 7. While maintaining the pH at that value, the suspension was heated in an oil bath at a temperature of 90° to 95° C for 2 hours. After cooling, the precipitated product was filtered, washed successively with chloroform and water and then dried over anhydrous magnesium sulfate to obtain 0.35 g of the above-tilted compound in an 80% yield.
IR Absorption Spectrum ν cm⁻¹: 1710 (CHO)
NMR Spectrum (CDCl$_3$) δ:
1.43 (doublet, 3H, J=6 Hz,

3.63 (quartet, 1H, J=6 Hz,

6.96 – 7.8 (multiplet, 9H, olefin, aromatic H) and 9.66 (singlet, 1H, —CHO).

d. (E)-2-[p-(β-2-Thienylvinyl)phenyl]propionic Acid 1 g of the (E)-2-[p-(β-2-thienylvinyl)phenyl]propanol obtained in (c) above was added to 10 ml of ethanol, and tetrahydrofuran was further added to form a solution. To this solution was added dropwise an aqueous solution of 1.4 g of silver nitrate in 28 ml of water. An aqueous solution of 0.55 g of sodium hydroxide in 28 ml of water was then added dropwise to the mixture. The reaction mixture was stirred at room temperature for 2 hours followed by working up in the same manner as described in Example 1 to obtain 0.853 g (80% yield) of the above-titled product, i.e., (E)-2-[p-(β-2-thienyl-vinyl)phenyl]propionic acid, having a melting point of 182°–183° C (recrystallized from n-hexane-diethyl ether, 2:1 by volume).
IR Absorption Spectrum ν cm⁻¹: 1700 (—COOH) and 2900–2500 (—COOH)
NMR Spectrum (CDCl$_3$) δ:
1.5 (doublet, 3H, J = 6Hz,

3.7 (quartet, 1H, J = 6Hz,

and
6.93 – 7.53 multiplet, 9H, olefin, aromatic H).
Elemental Analysis:
Calcd. for $C_{15}H_{14}O_2S$ (%): C 69.74; H 5.46.
Found (%): C 69.10; H 5.41.

EXAMPLE 3

Preparation of (E)-2-[p-(β-5-Chloro-2-thienylvinyl)phenyl]-propionic Acid a. Ethyl (E)-2-[p-(β-5l -Chloro-2-thienylvinyl)phenyl]-2,3-epoxybutyrate 4.0 g of (E)-2-(4-acetylstyryl)-5-chlorothiophene prepared as described in Reference Example 3 and 3.74 g of ethyl chloroacetate were dissolved in 112 ml of dry xylene and a solution of potassium t-butoxide prepared from 56 ml of t-butanol and 1.18 g of potassium metal was added dropwise to the solution over a period of 1.5 hours while cooling with ice in a nitrogen atmosphere. The resulting mixture was stirred for 24 hours and then warmed in a water bath for 2 hours. The t-butanol was then removed by distillation under reduced pressure and water was added to the residue. The mixture was extracted with diethyl ether, and the ethereal extract was washed with water and dried over anhydrous sodium sulfate. The ether was removed by distillation to obtain crude crystals which were then recrystallized from a mixture of n-hexane and methanol (1 : 1 by volume) to give 4.32 g (81.6% yield) of a fluffy yellow crystalline product having a melting point of 99° to 103° C and the following characterisitcs:
IR Absorption Spectrum ($ν_{max}^{KBr}$ cm⁻¹): (COOC$_2$H$_5$)
NMR Spectrum (CDCl$_3$) δ:
1.33 (t, J = 6 cps, COOCH$_2$CH$_3$),
1.50 (s, —COOC(CH$_3$)$_3$),
1.76 (s, β-CH$_3$),
3.43 (s, α-H),
4.3 (q, J = 6 cps, —COOCH$_2$CH$_3$)
The above data indicate that the resulting glycidic ester is a mixture of ethyl and butyl ester.

b. Sodium (E)-3-[p-(β-5-Chloro-2-thienylvinyl)phenyl]-2,3-epoxybutyrate

A solution of 0.25 g of sodium metal dissolved in 22.5 ml of ethanol was added to a solution of 2.56 g of glycidic ester of (E)-3-[p-(β-5-chloro-2-thienylvinyl)-phenyl]-2,3-epoxybutyrate prepared as described in (a) above while stirring, and 0.8 ml of water was then added to the mixture followed by stirring for 24 hours. The yellowish white precipitate formed was filtered, washed with water and air-dried to obtain 2.20 g (88% yield) of a white powdery product having a melting point of 215° C (with decomposition) and the following characteristics:
IR Absorption Spectrum ($ν_{max}^{KBr}$ cm⁻¹): 1600 (COONa)
The product thus obtained could be used in the subsequent step without further purification.

c. (E)-2-[p-(β-5-Chloro-2-thienylvinyl)phenyl]propanal 1.0 g of sodium (E)-3-[p-(β-5-chloro-2-thienylvinyl)-phenyl]-2,3-epoxybutyrate prepared as described in (c) above was suspended in 60 ml of water and the suspension was adjusted to pH 7 with dilute hydrochloric acid. After purging with nitrogen, the suspension was heated at 90° to 95° C for 2 hours thereby liberating CO$_2$ gas. Thereafter, the reaction mixture was cooled to precipitate crystals which were filtered and air-dried to give 0.78 g (97% yield) of a crude product having a melting point of 71° to 73° C and the following characteristics. The product thus obtained appeared unstable and was not further purified by recrystallization.

IR Absorption ($\nu_{max}^{KBr}$ cm$^{-1}$): 1710

NMR Spectrum (CDCl$_3$) δ:
 1.48 (3H, d, J = 6 cps, α-CH$_3$),
 3.63 (1H, q, J = 6 cps, α-H),
 6.66 –7.66 (8H, thiophene H, olefin H, phenyl H),
 9.66 (1H, d, J = 1 cps, —CHO)

d. (E)-2-[p-(β-5-Chloro-2-thienylvinyl)phenyl]propionic Acid 1.0 g of 18-Crown-6 (cyclic ether) and 1.22 g of silver nitrate were dissolved in 8 ml of ethanol and a solution of 1.0 g of (E)-2-[p-(β-5-chloro-2-thienylvinyl)phenyl]propanol dissolved in 8 ml of ethanol was then added thereto while stirring at room temperatures. Thereafter, a solution of 0.48 g of sodium hydroxide in 25 ml of water was added dropwise thereto over a period of 1 to 2 hours. After completion of the addition, the precipitated silver was filtered, and ethanol was removed from the filtrate by distillation under reduced pressure. Water was added to the resulting residue and the mixture was extracted with diethyl ether. Concentrated hydrochloric acid was added while cooling to the aqueous layer and the precipitate formed was then filtered and air-dried. Recrystallization from a mixture of n-hexane and ethyl acetate (1:1 by volume) yielded 0.4 g (38% yield) of a light yellowish white, granular product having a melting point of 147° to 150° C (with decomposition) and the following characteristics:

IR Absorption Spectrum ($\nu_{max}^{KBr}$ cm$^{-1}$):
 1690 (COOH),
 3300 – 2500 (COOH)

NMR Spectrum (CDCl$_3$) δ:
 1.53 (3H, d, J = 6 cps, αCH$_3$),
 3.76 (1H, q, J = 6 cps, α-H),
 6.83 – 7.53 (8H, m, olefin H, aromatic 4H, thiophene 2H)

Elemental Analysis
 Calcd. for C$_{15}$H$_{13}$O$_2$SCl: C 61.53; H 4.48.
 Found: C 61.68; H 4.44.

In the same manner as described in Examples 2 or 3, each of the following products of the formula (I) can also be produced from each of the starting materials of the formula (II).

| Starting Material of Formula (II) | Product of Formula (I) |
|---|---|
| (E)-2-(4-Acetylstyryl)-5-fluorothiophene | (E)-2-p-[β-(5-Fluoro-2-thienyl)vinyl]phenylpropionic acid |
| (E)-2-(4-Acetylstyryl)-5-bromothiophene | (E)-2-p-[β-(5-Bromo-2-thienyl)vinyl]phenylpropionic acid |
| (E)-2-(4-Acetylstyryl)-5-methylthiophene | (E)-2-p-[β-(5-Methyl-2-thienyl)vinyl]phenylpropionic acid |
| (E)-2-(4-Acetylstyryl)-5-ethylthiophene | (E)-2-p-[β-(5-Ethyl-2-thienyl)vinyl]phenylpropionic acid |
| (E)-2-(4-Acetylstyryl)-5-methoxythiophene | (E)-2-p-[β-(5-Methoxy-2-thienyl)vinyl]phenylpropionic acid |

EXAMPLE 4

Preparation of (E)-p-(β-2-Thienylvinyl)-phenylacetic Acid a. (E)-p-(β-2-Thienylvinyl)phenylacetothiomorpholide
 1 g of (E)-2-(4′-acetylstyryl)thiophene, 0.35 g of sulfur and 1.0 g of morpholine were mixed, and the resulting mixture was warmed on a steam bath for 3 to 4 hours. After formation of the precipitate, the reaction mixture was washed with ethyl acetate and any insoluble matter was recovered by filtration to obtain 1.3 g (90% yield) of the above-titled compound having a melting point of 115° C (recrystallized from ethyl acetate).

IR Absorption Spectrum $\nu$cm$^{-1}$:

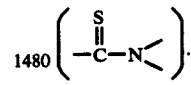

NMR Spectrum (CDCl$_3$) δ:
 3.16 – 4.00 (multiplet, 6H, —CH$_2$—,

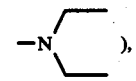

4.23 – 4.5 (multiplet, 4H,

and
 6.93 – 7.66 (multiplet, 9H, olefin, aromatic H).

b. (E)-p-(β-2-Thienylvinyl)phenylacetic Acid 1 g of the (E)-p-(β-2-thienylvinyl)phenylacetothiomorpholide obtained in (a) above was dissolved in 20 ml of dioxane, and an excess of a 10% aqueous solution of sodium hydroxide was added to the solution. The resulting mixture was refluxed on an oil bath at 110° C for 24 hours. The refluxed mixture was rendered acidic with a 10% hydrochloric acid, extracted with diethyl ether, washed with water and then dried over anhydrous magnesium sulfate to obtain 0.6 g (80% yield) of the above-titled product, i.e., (E)-p-(β-2-thienylvinyl)phenylacetic acid, as pale yellow grain-like crystals having a melting point of 177° to 178° C (recrystallized from diethyl ether-n-hexane, 1 : 2 by volume).

IR Absorption Spectrum $\nu$cm$^{-1}$:
 3000 – 2500 (OH)
 1700 –1690 (COOH)

NMR Spectrum (CDCl$_3$) δ:
 3.56 (singlet, 2H, —CH$_2$—)
 6.7 – 7.6 (multiplet, 9H, olefin, aromatic H).

Elemental Analysis:
 Calcd. for C$_{14}$H$_{12}$O$_2$S (%): C 68.83; H 4.95.
 Found (%): C 68.41; H 4.91.

EXAMPLE 5

Preparation of (E)-p-(β-5-Chloro-2-thienylvinyl)phenylacetic Acid a. (E)-p-(β-5-Chloro-2-thienylvinyl)phenylacetothiomorpholide 1.15 g of (E)-2-(4-acetylstyryl)-5-chlorothiophene prepared as described in Reference Example 3 was mixed thoroughly with 0.35 g of sulfur powder, and 0.76 g of morpholine was then added to the mixture. The resulting mixture was warmed on a water bath to dissolve the mixture followed by warming for 3 to 4 hours whereby the mixture solidified. After cooling, the resulting solid was dissolved in dichloromethane and the solution was subjected to silica gel column chromatography using dichloromethane as an eluant. Dichloromethane was then removed from the eluate by distillation and the residue thus obtained was recrystallized from ethyl acetate to obtain 1.12 g (70% yield) of the product as yellow granules having a melting point of 156° C and the following characteristics:

IR Absorption Spectrum $(\nu_{max}^{KBr}$ cm$^{-1}$: 1480 (C=S)
NMR Spectrum (CDCl$_3$) δ:
3.26 – 3.86 (6H, m, α-CH$_3$ +

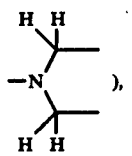
), 4.23 – 4.43 (4H, m,

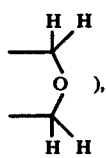
), 6.76 – 7.46 (8H, m, aromatic H, olefin H, thiophene H)
Elemental Analysis:
Calcd. for C$_{18}$H$_{18}$ONSCl: C 59.41; H 4.99; N 3.85.
Found: C 58.72; H 4.87; N 3.71.

b. (E)-p-(β-5-Chloro-2-thienylvinyl)phenylacetic Acid 1.0 g of (E)-p-(β-5-chloro-2-thienylvinyl)-phenylacetothiomorpholide prepared as described in (a) above was dissolved in 50 ml of dioxane and an excess amount of a 10% aqueous sodium hydroxide solution was added thereto. The mixture was then heated in an oil bath while refluxing at a temperature of 110° C for 24 hours. After completion of the reaction, dioxane was removed by distillation under reduced pressure and water was added to the residue. The resulting aqueous solution was rendered acidic with concentrated hydrochloric acid and extracted with diethyl ether. The extract was washed with water and dried over anhydrous magnesium sulfate. Diethyl ether was then removed by distillation to obtain crude crystals. Recrystallization from a mixture of ethyl acetate and n-hexane yielded 0.26 g (35% yield) of a product as yellow granules having a melting point of 175° to 176° C and the following characterisitcs:

IR Absorption Spectrum $(\nu_{max}^{KBr}$ cm$^{-1})$:
3000 – 2500 (COOH),
1680 (COOH)
NMR Spectrum (CDCl$_3$ + DMSO-d$_6$)δ:
3.56 (2H, s, α-CH$_3$),
6.8 – 7.53 (8H, m, olefin H, aromatic H, thiophene H)
Elemental Analysis:
Calcd. for C$_{14}$H$_{11}$O$_2$SCl: C 60.32; H 3.98.
Found: C 60.52; H 3.96.

In the same manner as described in Examples 4 or 5, each of the following compounds of the formula (I) can also be produced from each of the starting materials of the formula (II).

| Starting Material of Formula (II) | Compound of Formula (I) |
|---|---|
| (E)-2-(4-Acetylstyryl)-5-fluorothiophene | (E)-p-[β-(5-Fluoro-2-thienyl)vinyl]phenylacetic acid |
| (E)-2-(4-Acetylstyryl)-5-methylthiophene | (E)-p-[β-(5-Methyl-2-thienyl)vinyl]phenylacetic acid |
| (E)-2-(4-Acetylstyryl)-5-methoxythiophene | (E)-p-[β-(5-Methoxy-2-thienyl)vinyl]phenylacetic acid |
| (E)-2-(4-Acetylstyryl)-5-chlorofuran | (E)-p-[β-(5-Chloro-2-furyl)vinyl]phenylacetic acid |
| (E)-2-(4-Acetylstyryl)-5-nitrofuran | (E)-p-[β-(5-Nitro-2-furyl)vinyl]phenylacetic acid |
| (E)-2-(4-Acetylstyryl)-5-isopropylfuran | (E)-p-[β-(5-Isopropyl-2-furyl)vinyl]phenylacetic acid |
| (E)-2-(4-Acetylstyryl)furan | (E)-p-[β-(2-Furyl)vinyl]phenylacetic acid |

EXAMPLE 6

Preparation of
(E)-2-[p-(β-2-Thienylvinyl)-phenyl]propionic Acid a. Methyl (E)-p-(β-2-Thienylvinyl)phenylacetate 20 ml of diethyl ether was added to 1 g of the (E)-p-(β-2-thienylvinyl)phenylacetic acid prepared as described in Example 4, and tetrahydrofuran was further added thereto to form a solution. To the resulting solution was added 10 to 15 cc of etherial diazomethane which had been produced by hydrolyzing 10 g of N-nitrosomethylurea in 200 ml of diethyl ether using 60 ml of 40% potassium hydroxide followed by allowing the mixture to stand at room temperature for 1 hour. The diethyl ether was distilled off under reduced pressure to obtain white powdery crystals, which were then recrystallized from methanol to obtain 0.95 g (90% yield) of the above-titled compound as yellow grain-like crystals having a melting point of 82°– 84° C.

IR Absorption Spectrum νcm$^{-1}$: 1720 (—COOCH$_3$), —COOH disappear
NMR Spectrum (CDCl$_3$) δ:
3.60 (singlet, 2H, —CH$_2$—),
3.70 singlet, 3H, —OCH$_3$) and
6.96 – 7.53 (multiplet, 9H, olefin, aromatic H).

b. (E)-2-[p-(β-2-Thienylvinyl)phenyl]propionic Acid

A solution of 1.0 g of the above obtained methyl (E)-p-(β-2-thienylvinyl)phenylacetate in 2 ml of dimethylformamide was added dropwise to a suspension of 0.195 g of sodium hydride (a 50% dispersion in a mineral oil) in 1 ml of dimethylformamide at room temperature. After the resulting mixture was stirred for 3 to 5 hours, 5 ml of diglyme and 1.14 g of methyl iodide were added thereto followed by stirring for an additional 48 hours. After completion of the reaction, the reaction mixture was concentrated, and, after water was poured thereinto, was extracted with diethyl ether. The extract was washed with water and dried over MgSO$_4$ followed by distillation to remove the solvent. The residual oily substance was added to an ethanolic aqueous solution of an alkali (25 ml of ethanol, 10 ml of water and 1 g of sodium hydroxide), and the mixture was heated on a steam bath for 2 hours followed by distillation to remove the ethanol and water. The resulting solution was rendered acidic with concentrated hydrochloric acid and then extracted with diethyl ether. The extract was washed with water and dried over MgSO$_4$, and the solvent was distilled off to obtain crystals, which were then recrystallized from n-hexane-diethyl ether (2:1 by volume) to obtain 0.70 g (70% yield) of the above-titled product, i.e., (E)-2-[p-(β-2-thienylvinyl)phenyl]propionic acid, as white needles having a melting point of 182°– 183° C.

The IR absorption spectrum and the NMR spectrum of the product were found to be quite consistent with those of the product obtained in Example 2.

While the invention has been described in detail and with reference to specific embodiments thereof, it will be apparent to one skilled in the art that various changes and modifications can be made therein without departing from the spirit and scope thereof.

What is claimed is:

1. An (E)-2-[p-(β-substituted-vinyl)phenyl]alkanoic acid represented by the formula (I):

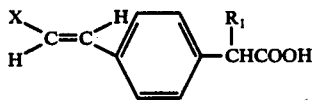     (I)

wherein $R_1$ represents a hydrogen atom, a methyl group or an ethyl group; and X represents a

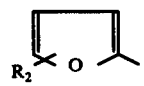

group or a

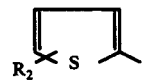

group, wherein $R_2$ represents a hydrogen atom, a nitro group, an amino group, a hydroxyl group, a halogen atom, an alkyl group having 1 to 4 carbon atoms or an alkoxy group having 1 to 4 carbon atoms, and the pharmaceutically acceptable salts thereof.

2. The (E)-2-[p-(β-substituted-vinyl)phenyl]alkanoic acid according to claim 1, wherein $R_1$ represents a hydrogen atom or a methyl group; and X represents a

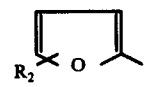

group, wherein $R_2$ represents a hydrogen atom, a nitro group, an amino group, a halogen atom, a methoxy group, or an alkyl group having 1 to 4 carbon atoms.

3. The (E)-2-[p-(β-substituted-vinyl)phenyl]alkanoic acid according to claim 2, wherein $R_2$ represents a hydrogen atom, a nitro group, a chlorine atom, a methyl group or an isopropyl group.

4. The (E)-2[p-(β-substituted-vinyl)phenyl]alkanoic acid according to claim 1, wherein $R_1$ represents a hydrogen atom or a methyl group, and X represents a

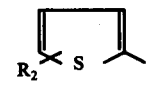

group, wherein $R_2$ represents a hydrogen atom, a fluorine atom, a chlorine atom, a bromine atom, an amino group, a methyl group, an ethyl group, a methoxy group or an ethoxy group.

5. The (E)-2-[p-(β-substituted-vinyl)phenyl]alkanoic acid according to claim 4, wherein $R_2$ represents a hydrogen atom, an amino group, a fluorine atom, a chlorine atom, a methyl group, or a methoxy group.

6. (E)-2-[p-(β-2-Furylvinyl)phenyl]propionic acid and a pharmaceutically acceptable salt thereof according to claim 1.

7. (E)-2-[p-(β-2-Thienylvinyl)phenyl]propionic acid and a pharmaceutically acceptable salt thereof according to claim 1.

8. (E)-p-(β-2-Thienylvinyl)phenylacetic acid and a pharmaceutically acceptable salt thereof according to claim 1.

9. (E)-2-[p-(β-5-Chloro-2-thienylvinyl)phenyl]-propionic acid and a pharmaceutically acceptable salt thereof according to claim 1.

10. (E)-p-(β-5-Chloro-2-thienylvinyl)phenylacetic acid and a pharmaceutically acceptable salt thereof according to claim 1.

* * * * *